United States Patent [19]

Morris

[11] 4,292,852

[45] Oct. 6, 1981

[54] METHOD AND APPARATUS FOR PHYSICALLY TESTING THE INTEGRITY OF THE CONNECTION BETWEEN AN ELECTRODE ASSEMBLY AND A TERMINAL CONDUCTOR OF AN ELECTROCHEMICAL CELL

[75] Inventor: Jesse L. Morris, Archer, Fla.

[73] Assignee: General Electric Company, Gainesville, Fla.

[21] Appl. No.: 116,844

[22] Filed: Jan. 30, 1980

[51] Int. Cl.³ ............................................. G01N 3/10
[52] U.S. Cl. ....................................... 73/827; 73/833
[58] Field of Search ................ 73/827, 831, 833, 834, 73/837; 429/90

[56] References Cited

U.S. PATENT DOCUMENTS 2,754,680 7/1956 Koehler ................................. 73/827

3,684,088 8/1972 Buttke et al. ......................... 73/827

*Primary Examiner*—Anthony V. Ciarlante
*Attorney, Agent, or Firm*—Morgan, Finnegan, Pine, Foley & Lee

[57] ABSTRACT

In the manufacture of electrochemical cells, the integrity of the mechanical joint between a coiled plate electrode assembly and a terminal conductor welded thereto is tested on the assembly line by applying to the terminal conductor a predetermined minimum tensile force tending to separate the conductor from the electrode assembly, while simultaneously restraining the coiled electrode assembly. Any movement of the conductor relative to the electrode assembly is sensed and, if movement exceeds a predetermined minimum value, the force on the conductor is automatically increased to a value sufficient to separate the poorly-connected conductor from the electrode assembly.

14 Claims, 6 Drawing Figures

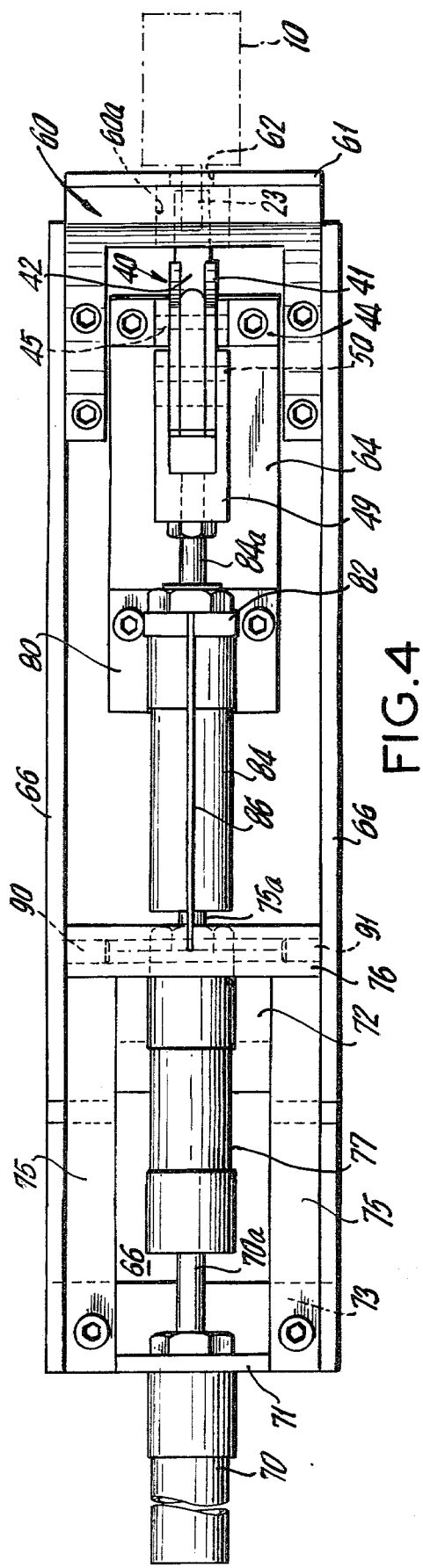
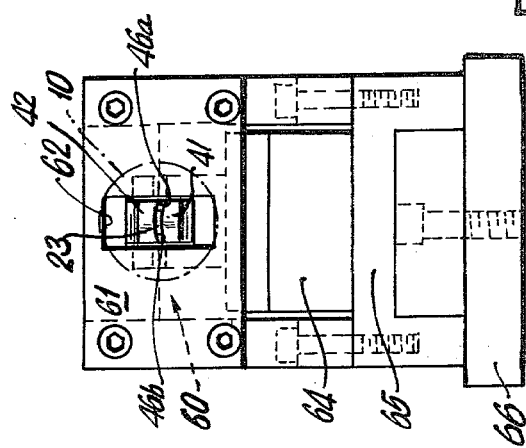

METHOD AND APPARATUS FOR PHYSICALLY TESTING THE INTEGRITY OF THE CONNECTION BETWEEN AN ELECTRODE ASSEMBLY AND A TERMINAL CONDUCTOR OF AN ELECTROCHEMICAL CELL

BACKGROUND OF THE INVENTION

This invention relates to the manufacture of electrode assemblies for electrochemical cells and, more specifically, to the testing of the joint formed between the electrode assembly for the cell and a terminal conductor attached to one of the cell electrodes.

Rechargeable electrochemical cells are made in many condfigurations. Most sealed electrochemical cells, however, are made by forming an electrode assembly comprised of interleaved positive and negative electrodes each separated from the other by a separator layer which is adapted to absorb and hold a liquid electrolyte, a metal container which serves as the negative terminal for the cell, a top cover which generally forms or contains the positive terminal for the cell, and a terminal conductor which electrically interconnects the positive electrode with the positive terminal of the cover or cover assembly.

There are several methods for connecting the terminal conductor between the electrode and external terminal. For example, a conductor tab can be formed integrally with the positive electrode, or it can be riveted or spot-welded to the edge of the electrode. Although this method of connection can be satisfactory, it is advantageous to have the terminal conductor contact the positive electrode at several points so as to obtain a better current distribution in the electrode by withdrawing current from the electrode at a few, and preferably several, points rather than at a single point as in the case of an integrally formed conductor tab. When the terminal connection is formed to provide several contact points with the electrode, it can be applied to the spirally-wound electrode assembly by percussion welding. A typical electrode assembly having attached thereto a terminal conductor tab is described in U.S. Pat. Nos. 3,695,935 and 4,029,856, both assigned to General Electric Company.

In some cell manufacturing methods, it has been the practice to weld the conductor tab to the exposed edges of the electrode assembly while it is held in a supporting nest used for winding electrodes. Thus, the individual positive and negative electrodes, together with a separator, are fed into the nest and wound by a retractable mandrel into the form of a spirally-wound coil. This nest is advanced stepwise from one position to the next along an assembly line where, ultimately, the electrode assembly is pushed into a metal casing. At one of the intermediate stations between the winding operation and the loading of the electrode assembly into the casing, the conductor tab is welded to the exposed edges of the positive electrode plate. Welding at this point in the manufacturing procedure is advantageous because the electrode assembly is already held in place and oriented to present to the welder the exposed electrode edges of the electrode.

Notwithstanding the use of automated transporting and welding equipment, a certain percentage of cells turn out defective. Operational defects are often traceable to a faulty weld joint between the conductor tab and the electrode. Even when the conductor tab is physically attached to the electrode, cell performance can vary from an acceptable standard. For example, "cold" joints can be encountered, bent or malformed conductor tabs can preclude the formation of a proper weld at all points desired, or welding at fewer than the desired number of crosspoints between the conductor and the electrode might result, thus producing variable internal cell impedance.

In the past, there was no satisfactory method or means for quickly checking the welds on each electrode assembly. Therefore, standard quality control methods were implemented. For example, only a small percentage of the cells were singled out for inspection and measurement. However, this inspection was usually visual only and, although it could isolate obvious weld defects, it did not expose more subtle weld problems such as the "cold" joint and insufficient weld area. Moreover, as stated above, visual inspection was done only on a sampled basis and would never detect faults with each and every cell.

In addition to visual inspection, it is the usual practice to electrically test each cell produced by applying a known current pulse to the cell and measuring its terminal voltage during and after the pulse. This electrical test is highly reliable; however, it is not conducted until much later in the manufacturing process, when the cell is already completed. Sometimes several tens, hundreds, or even thousands, of cells are manufactured before the first defective cell reaches the final performance test. If the defects are not detected prior to final assembly of the cells, all of the produced cells could be useless. On the other hand, although electrical continuity tests can be performed on the conductor tab-electrode assembly weld prior to final assembly, such electrical tests do not realiably reveal insufficient mechanical integrity of the weld. Even if a defective weld is detected, moreover, the conductor tab must be removed by hand in order to reuse the partially completed unit.

The present invention is aimed at a solution of the problem of controlling the quality of the production of electrochemical cells by early testing of the terminal connection between the electrode assembly and terminal conductor. In accordance with the invention, the integrity of the joint between the conductor and electrode assembly is tested by applying to the conductor, for a given time, a predetermined minimum tensile force tending to separate the conductor from the electrode assembly so as to establish thereby a minimum acceptable stress on the joint being tested. Any movement of the terminal conductor as a result of this force is detected, and an indication of unacceptability is provided when any such movement exceeds a predetermined distance corresponding to an insufficient mechanical integrity of the joint.

In the preferred embodiment to be described, a detected excess movement of the terminal conductor results in an electrical signal which causes the applied tensile force to increase to a level sufficient to completely separate the conductor from the electrode assembly, thus automatically removing the conductor defectively attached to the electrode assembly and permitting the recycling of the assembly in the manufacturing process. Equally important, however, is the fact that the defective attachment is detected substantially immediately.

BRIEF DESCRIPTION OF THE DRAWINGS

The following detailed description includes the drawings in which:

FIG. 4 is a plan view of the apparatus of FIG. 1;

FIG. 5 is a front elevational view of the apparatus; and

DESCRIPTION OF PREFERRED EMBODIMENTS

Figure 1:
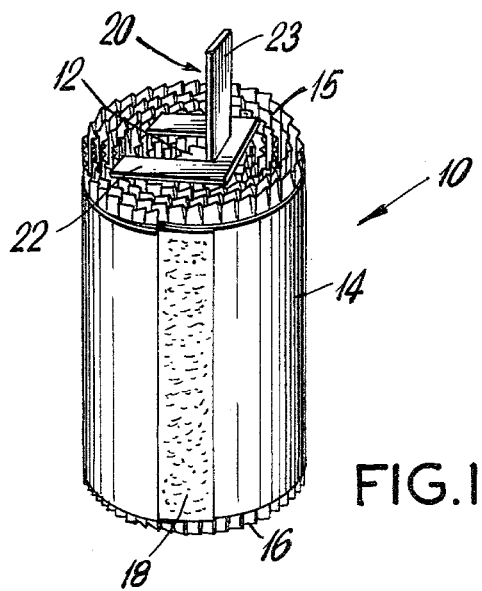
FIG. 1 is a perspective view of a typical electrode assembly which may be tested in accordance with the invention.

FIG. 1 shows the top end of a spirally-wound electrode assembly used in one common type of sealed nickel cadmium cell. This electrode assembly and the details of its manufacture may be found in U.S. Pat. No. 4,029,856.

As mentioned above, the spirally-wound electrode assembly comprises alternating positive and negative electrode plates and an electrolyte-absorbent separator layer, the plates and separator being wound into a spiral coil as shown in FIG. 1. The positive plate 12 is axially staggered upwardly from the negative plate 14 so that only the top edge of the positive plate is exposed at the top of the electrode coil, while only the coiled edge of the negative electrode is exposed at the bottom of the coil. The edge of the positive electrode 12 is rippled, or corrugated, at the top of the cell as shown at 15, the bottom edge of the negative plate 16 being similarly ruffled. These ruffled, or corrugated, edges 15, 16 of the plates provide mechanical rigidity to them. The separator layer is designated by the number 18 of FIG. 1 and, in practice, would ordinarily surround the entire outer convolution of the electrode assembly.

Welded to the exposed top ruffled edge 15 of the positive plate is a terminal conductor tab, designated generally by the numeral 20. This conductor 20 includes a U-shaped base portion 22 and an upwardly extending tab 23. The base portion is dimensioned to provide several crosspoints between the conductor 20 and edge 15 of the positive electrode 12, the tab 23 having a length enabling it to be subsequently welded to the underside of the cover assembly (not shown) which closes the top of the cell and contains the positive terminal. Co-pending application Ser. No. 55,978, filed July 9, 1979, discloses the apparatus and procedures used to achieve automatic final assembly of the cell, including the tab-to-cover welding operation just mentioned.

Figure 2:
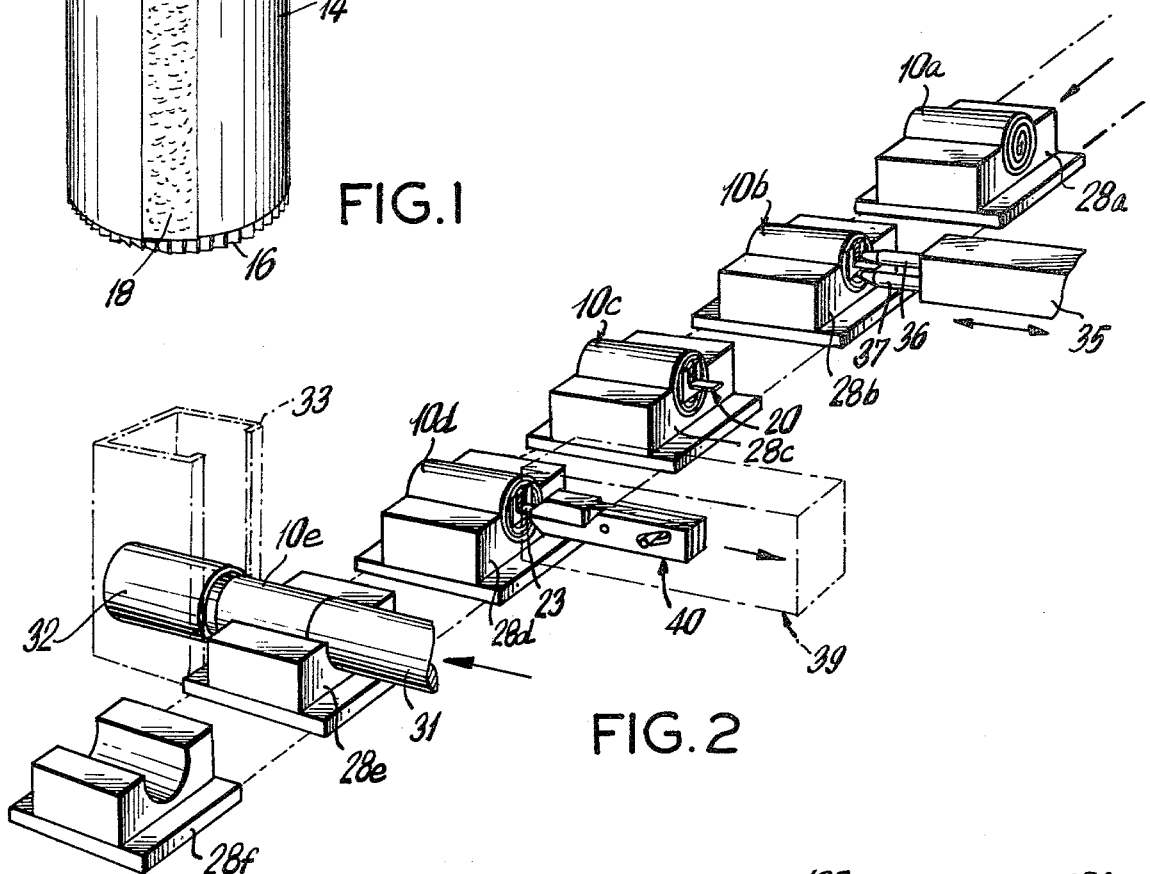
FIG. 2 is a schematic pictorial illustration of an assembly line carrying electrode assemblies which are to be tested in accordance with the invention.

FIG. 2 illustrates schematically a segment of the production line equipment which automatically winds the electrode plates into the spiral shape of FIG. 1, applies the terminal conductor 20 and stuffs the electrode assembly into the metal casing. A complete description of this equipment (omitting the welding step) may be found in co-pending application Ser. No. 73,087, filed Mar. 31, 1977 and assigned to General Electric Company. FIG. 2 is included here to explain better the environment in which the present invention finds application.

The production line assembly apparatus includes a plurality of winding nests 28a–28f . . . which are mounted on an endless conveyor chain (not shown but indicated by the phantom lines). These nests move in the direction shown by the arrows between a winding station (not shown) in which the two electrodes and separator layer are wound into the electrode coil, and an unloading station, occupied by nest 28e, in which the electrode coil is pushed by a ram 31 into the open end of a metal casing 32 that is fed automatically in a chute 33 to a location where it is properly aligned to receive the electrode coil 10e.

Nests 28 move intermittently, or stepwise, between the winding station and the unloading station. Nest 28a contains an electrode coil 10a prior to the application of a conductor tab 23 thereto, and the nest 28b is shown positioned at the station at which a conductor tab is welded to the exposed edges of the positive electrode coil. At this station a welding head 35 containing a weld electrode 36 and counterelectrode 37 percussion welds a terminal conductor 20 to the coiled electrode assembly. As is understood by those in the art, the welding head 35 includes means for receiving and moving the conductor 20, properly oriented, into physical and electrical contact with the exposed edges of the coiled positive electrode plate. When electrical contact is made, electrical current flows at the points of contact between the conductor base 22 (which is electrically contacted by the welding electrode 36) and the positive electrode (which is electrically contacted by the counterelectrode 37). The nest 28c contains an electrode assembly having welded thereto a terminal conductor 20.

The method and apparatus of the present invention are employed in the production process at the location occupied by the nest 28d for testing the weld joint between the conductor 20 and the coiled edge 15 of the positive electrode. The apparatus, schematically depicted by the dashed outline 39, includes conductor grasping means in the form of a pair of jaws 40 which grasps the conductor tab 23 and exerts on it a predetermined tensile force. If the welded terminal conductor 20 withstands this force, the weld is deemed satifactory and the electrode assembly, with its associated conductor, is subsequently loaded into the metallic casing as, for example, at a location represented by the nest 28e. Of course, should the welded terminal conductor 20 fail the test to which it is subjected by the test apparatus 39, the electrode assembly is not loaded into a metal casing but, instead, traverses the station-loading operation and is removed at a separate location, e.g., that occupied by empty nest 28f.

Figure 3:
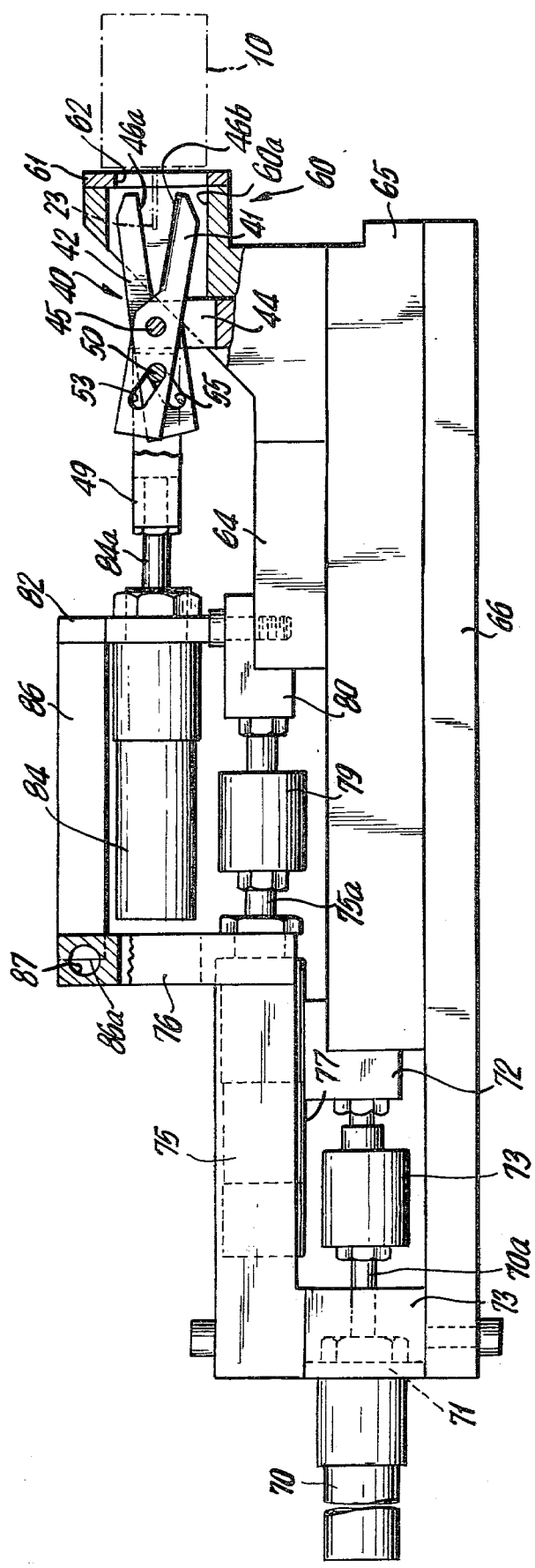
FIG. 3 is a side elevation view of apparatus constructed according to the invention for performing the test.

Referring now to FIGS. 3–5, showing in detail the test apparatus of the present invention, the jaws 40, illustrated in FIG. 2, are seen more clearly. Jaw assembly 40 is comprised of a lower jaw 41 and an upper jaw 42. These jaws are pivotally supported in a bracket 44 for scissors-like motion between an open position (illustrated in the drawings) and a closed, conductor-engaging position. Preferably, the jaws provide mating curved surfaces 46a, 46b which deform the conductor tab slightly and thereby rigidify it when the jaws 40 close.

Jaws 40 are operated by the axial movement of a clevis 49 which carries a dowel 50 extending through its two arms and through angled slots 53 in the arms 41a, 41b of the lower jaw and the oppositely angled slot 55 of the upper jaw. The surfaces of slots 53, 55 in the jaws form camming surfaces against which the clevis dowel 50 acts when moved axially (i.e. parallel to the longitudinal axis of the jaws). When the clevis is moved forwardly to the position shown in FIGS. 3 and 4, the dowel 50, riding against the surfaces of slots 53, 55, urges the jaws open. When clevis 49 is retracted, dowel 50 moves backwardly and jaws 41, 42 are cammed into the closed, tab-engaging position. Preferably, the jaws are completely closed prior to the rearward limit of travel for dowel 50. In this manner, the closing pressure can be regulated by regulating the rearward pull force on dowel 50.

After the jaw assembly has closed about the tab 23, it is pulled backwardly. However, during the time that jaws 40 are exerting a tensile pull force on the conductor tab 23, the electrode coil 10 is restrained against movement in the direction of the pull force. To that end, a restraining member 60, generally having a U-shaped yoke configuration, is used. Member 60 is formed with a rectangular channel 60a for receiving the jaw pair 40. Attached to the front of restraining member 60 is a restraining plate 61 having a rectangular opening 62 formed therein for receiving the terminal conductor of the cell. The dimensions of opening 62 are smaller than the channel 60a. The restraining member 60 is mounted on an axially movable slide 64. This slide 64 is, in turn, carried on a larger, axially movable slide 65, the latter being supported by main base plate 66. Base plate 66 is fixedly mounted closely adjacent the path of travel of electrode coils as they are transported by winding nests 28.

All components of the apparatus are operated by air cylinder actuators. Thus, slide 65, to which is mounted restraining member 60, is moved between the forward position (as illustrated), in which the restraining member 60 is positioned adjacent the end of electrode assembly 10, and a retracted position, in which the front surface of restraining plate 61 is positioned rearwardly of the tab 23 in order to permit cell assemblies 10 to move transversely past the testing station. Movement of the slide 65 is controlled by actuator 70, mounted on a U-shaped rear bracket 71 screwed to the bore plate. The piston 70a of the actuator is coupled to a bracket at the rear of the slide 65 through an alignment fixture 73.

Attached to the sides of the bracket 71 are horizontally extending support arms 75 cantilevered forwardly for supporting a vertical mounting plate 76 carrying a second air cylinder actuator 77. This cylinder moves the top slide 64 between a forward position (as illustrated) in which jaws 40 are positioned for capturing and pulling the conductor tab 23, and a rearward position, in which jaws 40 are clear of tab 23 in order to permit transverse conveyance of electrode assemblies 10 on the assembly line without interference. The actuator shaft 75a is coupled via an alignment fixture 79 (e.g. Tom Thum Model 250) to the mounting piece 80 affixed to the back end of slide 64. Alignment fixtures 73 and 79 are direct coupling devices which transmit axial motion to their output shafts, notwithstanding misalignments between the actuator shafts (70a, 75a) and the slides (64, 65).

Mounting piece 80 also includes a vertically extending bracket 82 that carries air cylinder actuator 84, the piston 84a of which is affixed to clevis 49. When the actuator 84 is energized, the piston 84a retracts to close jaws 40 on conductor tab 23. As earlier mentioned, the air pressure to this actuator may be regulated, set or otherwise controlled so that the closing pressure on the jaws can be increased or decreased, as desired.

Also affixed to the vertical bracket 82, and extending rearwardly from the top thereof, is an indicator rod 86. This indicator rod moves with the slide 64 and, thus, with any axial movement of jaws 40 relative to the base plate 66. This slide is terminated at end 86a which intercepts a bore 87 in the vertical bracket 76. Referring to FIG. 4, a light source 90 is mounted in one end of the bore so as to direct a beam of light toward a photodetector 91 at the other end of the bore. Under ordinary circumstances, when the jaws 40 have been moved to the forward position and closed about the conductor tab 23, light from source 90 reaches photodetector 91. However, when indicator rod 86 moves back by an amount sufficient to diminish the light reaching photodetector 91, a signal is developed which is used to indicate a defective weld joint between the base 22 of the terminal conductor and the cell assembly 10.

Figure 6:
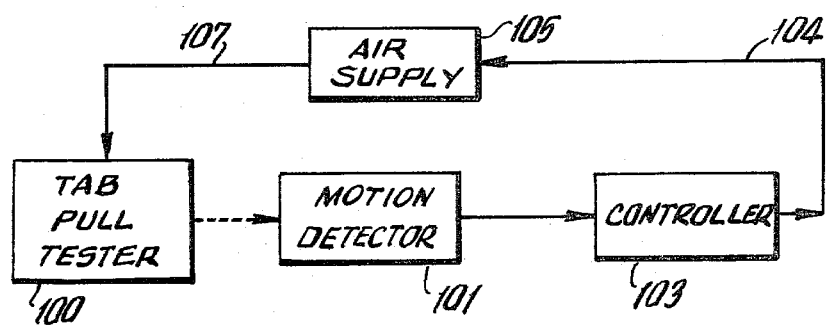
FIG. 6 is a schematic block diagram of the signal path associated with the testing operation performed.

Turning to FIG. 6, the conductor tab pull testing apparatus of FIGS. 3–5 is represented by the block 100. The movement photosensor, which includes light source 90 and photodetector 91, is represented by the block 101, the dashed line between these two units indicating the responsiveness of detector 101 to the components in the tester (e.g., indicator rod 86). An electrical signal from the detector 101 is fed to a digital controller 103. This controller may be any suitable commercial unit, for example, the Texas Instrument Co. TI 5 Controller. It has the capacity for receiving a number of input signals and developing either analog or digital output signals in response to such input signals. In the present system, controller 103 produces signals which, in the first instance, extend and retract the air cylinder actuators 70, 77, 84 in a predetermined sequence that is synchronized with the movement of the electrode assemblies in nests 28. Thus, the air cylinder actuators are energized during the dwell time between advancement of the nests from one station to the next.

When a signal is received from detector 101 indicating that the terminal conductor 20, under the predetermined tensile force applied to the jaws 40, has moved in excess of a predetermined amount, the controller 103 provides a signal to elements of the air supply system 105, which may include air valves, to increase the air pressure driving the air cylinder actuator 77. This causes slide 64 (and jaws 40) to be moved in the backward direction under greater force, this force being preset to a value sufficient to completely separate and remove the terminal conductor from the electrode assembly 10. In actual practice, this result is achieved by supplying the actuator 77 with air from two selectable air lines at different pressures. These lines may be connected to a common air source; one line, however, includes an air pressure regulator (not shown) whose air output is at a lower pressure. The output line 107 from air supply 105 represents the air at one or more pressures supplied to the air cylinder actuators.

In operation, controller 103 develops the requisite signals required by the air supply 105, and provides the slide movement signals over signal output lines 104 during times when the nests 28 are stationary. The stationary, or dwell, time is typically on the order of 1–2 seconds. Air initially is supplied to the actuator 70 to move slide 65 forwardly and position the restraining plate 61 against the coiled edge 15 of an electrode assembly 10d. Immediately thereafter, air is routed to the cylinder actuator 77 to move the slide 64 into its forward position (FIG. 3). This places the tab grasping jaws 40 into general vertical alignment with tab 23.

Thereupon, the cylinder actuator 84 is energized so as to retract the clevis 49 and close the jaws 40 about the conductor tab 23.

With the jaws tightly closed on tab 23, the double acting cylinder 77 is now retracted upon being supplied with air at a predetermined regulated pressure. This applies a predetermined tensile force to the conductor tab, tending to separate it from the electrode assembly. If the weld joint between the terminal conductor and the assembly has an acceptable mechanical integrity, there will be no appreciable pulling away of the tab from the assembly during the allotted time, and no excessive motion of the indicator rod 86 will be sensed by the detector means 90, 91. In this case, the air pressure to the cylinder 77 is released, the air cylinder actuator 84 is reversed to open jaws 40, whereupon the air cylinders 70 and 77 are energized to retract the slides 64 and 65. The electrode assemblies are now ready for advancement to their next positions, after which the test is repeated on the next succeeding cell.

If, in the course of applying a tensile force to the conductor tab 23, an excessive amount of backward motion of the jaws 40 occurs as a result of the tab being pulled away from its welded joint, the rod 86 moves backwardly, diminishing the light reaching detector 91 from the source 90 and thus producing an electrical signal which causes the controller 103 to activate the high pressure air supplied to the air cylinder 77. This will cause the jaws 40 to pull on the tab 23 with sufficient force to tear the terminal conductor 20 off the electrode assembly. This permits the electrode assembly to be reused, and also enables the assembly line to sense automatically, at a downstream location, the absence of a terminal conductor and thus allow that particular electrode assembly to bypass the casing loading operation at the position of nest 28e (FIG. 2).

In sum, by physically testing the integrity of the mechanical connection between the terminal conductor 20 and the electrode assembly 10 in the manner described above, it is possible to check the electrical integrity, as well as the physical integrity of the connection. That is to say, the ability of the terminal conductor to withstand a predetermined tensile force is a measure of the area of the weld joint, and thus the area of the current carrying transfer points, between the terminal conductor and the edges of the exposed electrode coil. Additionally, by applying tensile force to the conductor tab, minor misalignments of the conductor tab can be corrected by the tensile force, while simultaneously rigidifying the conductor tab. While it is an optional feature of the invention, a defective tab can be removed by the tab pull tester apparatus, thus permitting the relatively expensive electrode assembly to be recycled.

Although the invention has been described with reference to the preferred embodiments, it is clear that several modifications and variations can take place without departing from the spirit and scope of the invention. For example, the use of conductor grasping means in the form of a scissors-like jaw is preferred because of its simplicity; however, other types of conductor-engaging means can be used. Also, while I have found it preferable to be able to actuate the restraining means and the conductor grasping means independently of one another, these two elements could be combined into a single unit, or be mounted on a common slide, should that be desired. As another example of alterations which may be made, several types of movement detectors may be employed. I have found the photoresponsive detector to be effective, but mechanical detectors and other types of electrical detectors (e.g., a magnetic switch) can be employed. Likewise, other types of actuators can be used. For example, mechanical, rather than pneumatic, actuators are workable with the invention. Accordingly, all such modifications and variations, of whatever form and nature, and except as otherwise expressly excluded, are intended to be included within the scope of the appended claims.

What is claimed is:

1. In the manufacture of electrochemical cells having an electrode assembly and a terminal conductor physically joined thereto, a method for testing the integrity of the joint between the terminal conductor and the electrode assembly, comprising:

exerting a predetermined minimum tensile force on said conductor, tending to separate the conductor from the electrode assembly so as to establish a minimum acceptable stress on the joint being tested;

detecting movement of the terminal conductor relative to the electrode assembly; and providing an indication of unacceptability when such movement exceeds a predetermined distance corresponding to insufficient mechanical integrity of the joint.

2. The method of claim 1, wherein:

the electrode assembly comprises at least one electrode wound in a spiral coil, and the conductor extends from the spiral edge of the electrode coil;

the method including the step of restraining the end of said coil against movement during application of said force to the terminal conductor.

3. In the manufacture of electrochemical cells of the type having a spirally-wound electrode assembly and an electrode terminal conductor mechanically joined to an end of an electrode in the electrode assembly, wherein electrode assemblies are carried by support means seriatim for stepwise advancement along a production line, a method for testing the integrity of the joint between the terminal conductor and electrode assembly, comprising:

grasping said terminal conductor while said electrode assembly is carried in the advancing support means;

pulling with a predetermined minimum force on said terminal conductor, while restraining the electrode assembly against axial movement thereof so as to establish at the joint being tested a minimum acceptable stress;

detecting movement of the terminal conductor relative to the restrained electrode assembly; and providing an indication when said movement exceeds a predetermined distance.

4. The method of claim 3, further comprising:

increasing the pulling force, in response to said indication, to a level sufficient to separate said terminal conductor from the electrode assembly.

5. Apparatus for physically testing the mechanical integrity of the joint formed between an electrode of an electrode assembly for an electrochemical cell and a terminal conductor attached thereto, comprising:

a restraining member;

means for controllably positioning said restraining member adjacent the electrode assembly for restraining movement thereof;

conductor grasping means selectively operable between a conductor-holding condition and a conductor-disengaging condition;

means for exerting on said grasping means when in the conductor-holding condition a predetermined minimum force tending to move said grasping means in a direction away from the electrode assembly, thereby creating a predetermined minimum acceptable stress on the joint being tested; and detector means responsive to movement of said grasping means, relative to the electrode assembly, as a result of the force exerted thereon for providing an indication when any such movement exceeds a predetermined distance.

6. Apparatus according to claim 5, further comprising:

means responsive to the detector means for causing the force exerted by said grasping means to increase to a value sufficient to separate the conductor from the electrode assembly when movement of the terminal conductor exceeds said predetermined distance.

7. Apparatus according to claim 5, wherein the electrode assembly comprises at least one spirally-wound electrode and a terminal conductor is joined to the edge of said electrode, said restraining member being positionable against said edge of the spirally-wound electrode.

8. Apparatus according to claim 7, wherein:

said positioning means comprises a slidable carriage movable between a disengaged position, in which the restraining member is free of the electrode assembly and terminal conductor, and an engaged position in which the restraining member is closely adjacent the edge portions of the spirally-wound electrode, thereby to restrain it against movement along the axis thereof when said grasping means exerts stress on said joint.

9. Apparatus according to claim 5, wherein:

said grasping means comprises a slidable carriage controllably movable between a first position free of the electrode assembly and terminal conductor, and a second position in which the terminal conductor is engageable by the grasping means when it is in the conductor-holding condition.

10. Apparatus according to claim 5, wherein said grasping means includes:

a pair of jaws movable between a closed position, in which the terminal conductor is fixedly held between said jaws, and an open position in which said jaws release the terminal conductor.

11. Apparatus according to claim 10, wherein said grasping means further includes:

a bracket supporting at least one of said jaws about a pivot point for scissors-like motion between the open and closed positions, said movable jaw having a camming surface thereon; and means carrying a camming member engaging said camming surface and movable between first and second positions for opening and closing said jaws by camming action.

12. Apparatus according to claim 11, wherein:

said jaws have conductor-grasping surfaces which are curved so as to rigidify said conductor by deforming it in conformity with the curved surfaces of said jaws upon the closing thereof.

13. Apparatus for physically testing the mechanical integrity of the joint formed between an electrode for an electrochemical cell and a terminal conductor mechanically attached thereto, comprising:

a first carriage having mounted thereto a restraining member, said carriage being controllably movable between a first position wherein said restraining member is remote from the electrode and a second position in which said restraining member is positioned closely adjacent the electrode so as to prevent longitudinal movement thereof;

terminal conductor grasping means operable between a conductor-engaging condition, in which said conductor is fixedly held, and a disengaged condition in which said conductor is released;

a second carriage slidably movable between a withdrawn position, in which the electrode and terminal conductor are free of said grasping means, and a longitudinally forward, operative position in which said conductor-grasping means may engage the conductor, said first and second carriage means being slidably movable independently of each other; and first and second actuator means connected to said first and second carriages, respectively, for independently and controllably moving each thereof.

14. A system for physically testing the mechanical integrity of the joint formed between a terminal conductor and an electrode assembly for an electrochemical cell, while said electrode assembly is in an assembly line, comprising:

means for supporting and conveying a plurality of such electrode assemblies stepwise along an assembly line past a test station; and testing means at said test station, said testing means having a restraining member controllably movable between a first position free of the path of movement of electrode assemblies along the assembly line, and a second position closely adjacent the electrode assembly to preclude forward movement thereof, terminal conductor grasping means operable between an engaged condition, in which the conductor is fixedly held, and a disengaged condition, in which the conductor is unrestrained, and including means for exerting a predetermined minimum axial force thereon tending to separate the conductor from the electrode assembly so as to establish a minimum acceptable stress on the joint being tested, and means responsive to a movement of said grasping means as a result of said axial force for providing an indication of unacceptability when such movement exceeds a predetermined distance.

* * * * *